(12) United States Patent  
Qu et al.

(10) Patent No.: US 8,311,620 B2
(45) Date of Patent: Nov. 13, 2012

(54) METHODS AND APPARATUS TO TREAT AND PREVENT ATRIAL TACHYARRHYTHMIAS

(75) Inventors: Jihong Qu, Maple Grove, MN (US); Haris J. Sih, Minneapolis, MN (US); Mark Schwartz, White Bear Lake, MN (US); Prashant Sinha, West NY, NJ (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 92 days.

(21) Appl. No.: 11/895,025

(22) Filed: Aug. 22, 2007

(65) Prior Publication Data

US 2009/0054943 A1    Feb. 26, 2009

(51) Int. Cl.
*A61B 5/04* (2006.01)
*A61K 9/22* (2006.01)

(52) U.S. Cl. ............... 600/518; 604/890.1; 604/503; 607/3; 607/4; 607/5; 607/9

(58) Field of Classification Search ........... 604/890.1, 604/503, 66; 607/3, 62, 4, 5, 9; 600/509, 600/515, 518
See application file for complete search history.

(56) References Cited

U.S. PATENT DOCUMENTS

| 4,146,029 | A | * | 3/1979 | Ellinwood, Jr. | 604/891.1 |
| 5,690,682 | A | * | 11/1997 | Buscemi et al. | 607/3 |
| 6,968,226 | B2 | * | 11/2005 | Mehra et al. | 600/509 |
| 7,034,008 | B2 | | 4/2006 | Donahue et al. | |
| 2002/0155101 | A1 | * | 10/2002 | Donahue et al. | 424/93.21 |
| 2003/0204206 | A1 | * | 10/2003 | Padua et al. | 607/2 |
| 2004/0029148 | A1 | | 2/2004 | Feld et al. | |
| 2005/0021089 | A1 | | 1/2005 | Sharma | |
| 2005/0192637 | A1 | | 9/2005 | Girouard et al. | |
| 2006/0015146 | A1 | | 1/2006 | Girouard et al. | |
| 2006/0134071 | A1 | | 6/2006 | Ross et al. | |
| 2007/0190028 | A1 | | 8/2007 | Qu et al. | |
| 2008/0183228 | A1 | | 7/2008 | Kim et al. | |

FOREIGN PATENT DOCUMENTS

WO    WO-2009/025812 A2    2/2009

(Continued)

OTHER PUBLICATIONS

"Heart", [online]. [retrieved Nov. 21, 2006]. Retrieved from the Internet: <http://simple.wikipedia/org/wiki/Heart>, 3 pgs.

(Continued)

*Primary Examiner* — Mark W Bockelman
(74) *Attorney, Agent, or Firm* — Schwegman Lundberg & Woessner, P.A.

(57) ABSTRACT

The invention provides a cardiac rhythm management system which includes a tachyarrhythmia detection and classification circuit programmed to detect and classify a tachyarrhythmia, a biologic therapy delivery device configured to deliver or regulate an expression cassette suitable for terminating or preventing atrial fibrillation (AF), and a control circuit coupled to the tachyarrhythmia detection and classification circuit and the biologic therapy delivery device. Also provided is an implantable medical device for use in a body having a cardiovascular system, which includes an implantable device body including at least a cardiovascular portion configured to be in the cardiovascular system, and an expression cassette incorporated into the cardiovascular portion of the implantable device body, the expression cassette selected to express a gene product that terminates or prevents AF. Further provided are methods which employ particular expression cassettes to prevent, inhibit or treat AF.

21 Claims, 4 Drawing Sheets

FOREIGN PATENT DOCUMENTS

WO  WO-2009025812 A3  2/2009

OTHER PUBLICATIONS

"International Application Serial No. PCT/US2008/009898, International Search Report mailed Mar. 24, 2009", 5 pgs.

"International Application Serial No. PCT/US2008/009898, Written Opinion mailed Mar. 24, 2009", 10 pgs.

Donahue, J. K., et al., "Focal Modification of Electrical Conduction in the Heart by Viral Gene Transfer", *Nature Medicine*, 6(12), (2000), 1395-1398.

Gaborit, N., et al., "Human Atrial ion Channel and Transporter Sub-unit Gene-Expression Remodeling Associated With Valvular Heart Disease and Atrial Fibrillation", *Circulation*, 112(4), (2005), 471-81.

Gollob, M. H., et al., "Somatic Mutations in the Connexin 40 Gene (GJA5) in Atrial Fibrillation", *N Engl J Med.*, 354(25), (2006), 2677-88.

Hajjar, R. J., et al., "Modulation of Ventricular Function Through Gene Transfer in vivo", *Proc Natl Acad Sci USA*, 95, (1998), 5251-5256.

Hajjar, R. J., et al., "Prospects for Gene Therapy for Heart Failure", *Circulation Research*, 86(6), (2000), 616-621.

Hallahan, D. E., et al., "Spatial and Temporal Control of Gene Therapy Using Ionizing Radiation", *Nature Medicine*, 1(8), (1995), 786-791.

Hoshijima, M., et al., "Chronic Suppression of Heart-Failure Progression by a Pseudophosphorylated Mutant of Phospholamban via in vivo Cardiac rAAV Gene Delivery", *Nature Medicine*, 8(8), (2002), 864-871.

Isner, J. M, "Myocardial Gene Therapy", *Nature*, 415(6868), (2002), 234-239.

Kikuchi, K., "Targeted Modification of Atrial Electrophysiology by Homogeneous Transmural Atrial Gene Transfer", *Circulation*, 111(3), (2005), 264-70.

Lee, L. Y., et al., "Exogenous Control of Cardiac Gene Therapy: Evidence of Regulated Myocardial Transgene Expression After Adenovirus and Adeno-Associated Virus Transfer of Expression Cassettes Containing Corticosteroid Response Element Promoters", *The Journal of Thoracic and Cardiovascular Surgery*, 118, (1999), 26-35.

Lin, H., et al., "Regulating Genes with Electromagnetic Response Elements", *Journal of Cellular Biochemistry*, 81, (2001), 143-148.

Lin, H., et al., "Specific Region of the *c-myc* Promoter is Responsive to Electric and Magnetic Fields", *Journal of Cellular Biochemistry*, 54, (1994), 281-288.

Olson, T. M., et al., "Kv1.5 channelopathy due to *KCNA5* loss-of-function mutation causes human atrial fibrillation", *Human Molecular Genetics*, 15(14), (2006), 2185-2191.

Regan, C. P., et al., "In Vivo Cardiac Electrophysiologic Effects of a Novel Diphenylphosphine Oxide $I_{Kur}$ Blocker, (2-Isopropyl-5-methylcyclohexyl) Diphenylphosphine Oxide, in Rat and Nonhuman Pimate.", *J Pharmacol Exp Ther.*, 316(1), (2006), 727-732.

Rubenstrunk, A., et al., "Transcriptional Activation of the Metallothionein I Gene by Electric Pulses in vivo: Basis for the Development of a New Gene Switch System", *The Journal of Gene Medicine*, 5, (2003), 773-783.

Semenza, G. L., "Hypoxia-inducible nuclear factors bind to an enhancer element located 3' to the human erythropoietin gen", *Proc Natl Acad Sci USA*, 88(13), (1991), 5680-5684.

Semenza, G. L., "Transcriptional Regulation of Genes Encoding Glycolytic Enzymes by Hypoxia-Inducible Factor 1", *The Journal of Biological Chemistry*, 269(38), (1994), 23757-23763.

Shimizu-Sato, S., et al., "A Light-Switchable Gene Promoter System", *Nature Biotechnology*, 20, (2002), 1041-1044.

Suzuki, M., et al., "Regulatable Promoters for Use in Gene Therapy Applications: Modification of the 5'-Flanking Region of the CFTR Gene with Multiple cAMP Response Elements to Support Basal, Low-Level Gene Expression That Can Be Upregulated by Exogenous Agents That Raise Int", *Human Gene Therapy*, 7, (1996), 1883-1893.

Tavi, P., et al., "Pacing-induced calcineurin activation controls cardiac $Ca^{2+}$ signalling and gene expression", *J Physiol.*, 554(Pt 2), (Jan. 15, 2004), 309-20.

Van Wagoner, D. R., et al., "Pharmacologic relevance of $K^{+C}$ Channel Remodeling in Atrial Fibrillation", *J Mol Cell Cardiol.*, 32(10), (2000), 1763-1766.

Yamashita, T., et al., "Short-Term Effects of Rapid Pacing on mRNA Level of Voltage-Dependent $K^+$ Channels in Rat Atrium—Electrical Remodeling in Paroxysmal Atrial Tachycardia", *Circulation*, 101, (2000), 2007-2014.

"Japanese Application Serial No. 2010-521870, Office Action mailed Jan. 26, 2012", (w/ English Translation), 7 pgs.

"Japanese Application Serial No. 2010-521870, Response filed Apr. 18, 2012 to Office Action mailed Jan. 26, 2012", 11 pgs.

\* cited by examiner

METHODS AND APPARATUS TO TREAT AND PREVENT ATRIAL TACHYARRHYTHMIAS

BACKGROUND

Atrial tachyarrhythmias (AT) affect many people and the quality of their lives. For instance, atrial fibrillation (AF) affects an estimated 2.3 million people in the United States. AF is a condition in which control of heart rhythm is taken away from the normal sinus node pacemaker by rapid activity (400-600 pulses per minute in humans versus about 60 beats/minute at rest or 180-200 beats/minute at peak exercise) in different areas within the upper chambers (atria) of the heart. This results in rapid and irregular atrial activity and, instead of contracting, the atria quiver. It is the most common chronic cardiac rhythm disturbance in humans and represents a major clinical problem with serious morbidity and mortality. AF requires a trigger and an atrial substrate to perpetuate AF. Eliminating the trigger or altering the substrate may reduce the incidence of AF. A substrate that perpetuates AF may involve the wavelength (conduction velocity, CV; and effective refractory period, ERP). Altering either CV or ERP may change the substrate necessary to maintain AF. Moreover, short atrial ERPs contribute to the substrate for multiple reentrant wavelets that sustain AF.

Pharmacological and device therapies have not been satisfactory to treat AF, as they have varying degrees of efficacy as well as side effects and complications. Cardiac arrhythmias have been treated traditionally with antiarrhythmic drugs that control the rhythm by altering cardiac electrical properties. However, the available drugs are not specific for atrial electrical activity and can have profound effects on ventricular electrophysiology. For example, K channel blocking drugs that are used to treat AF can mimic potentially lethal congenital disorders of the cardiac repolarization (Such as "torsade-de-pointes"). Moreover, it has become apparent over the last 20 years that the effects of antiarrhythmic drugs on the electrophysiology of the ventricles can themselves paradoxically lead to life-threatening rhythm disorders (proarrhythmia) and increase mortality. Further, drug therapy has only about 60% efficacy. There has been, therefore, a shift towards non-pharmacological therapies for cardiac arrhythmias, including controlled destruction of tissue generating or propagating arrhythmias ("ablation therapy") and implantable devices that can sense arrhythmias and terminate them with controlled electrical, discharges. However, catheter-based therapies are potentially dangerous and highly variable. In contrast to other cardiac arrhythmias, AF continues to be challenge for both pharmacological and non-pharmacological approaches to treatment.

SUMMARY OF THE INVENTION

The invention provides methods, devices, and systems to alter an atrial fibrillation trigger or substrate, thereby preventing, inhibiting or treating AF. The methods may employ vectors to deliver expression cassettes having nucleic acid sequences for a gene product corresponding to an ion channel protein or gap junction, e.g., sense or antisense Kv1.5, Kir2.1, or connexin sequences, that alters ion channel or gap junction level or activity. In one embodiment, expression of the nucleic acid sequence in the expression cassette in the atria decreases $I_{Kur}$, $I_{K1}$ or $I_f$, or prolongs action potential duration (APD) and/or effective refractory period (ERP). In one embodiment, Kir2.1 ($I_{K1}$) downregulation may lengthen APD and/or ERP. In one embodiment, Kv1.5 downregulation may lengthen APD and/or ERP, as Kv1.5 ($I_{Kur}$) is only expressed in human atria, and so may be a unique target for AF therapy with the additional benefit that altering Kv1.5 does not affect ventricular electrophysiology. In one embodiment, an afflicted or susceptible AF substrate is modified by delivering genes encoding wild-type Cx40 or a dominant negative of $I_{Kur}$, or a genetic inhibitor of $I_{Kur}$, e.g., Kv1.5 siRNA or antisense sequences, or delivering an antibody that suppresses $I_{Kur}$ or $I_{K1}$. The delivery of agents that inhibit expression or activity of certain gene products, inhibits AF, e.g., by lowering the susceptibility to the triggers for AF.

The vectors may be delivered systemically, for example, a viral vector may be administered to the coronary artery of a mammal. In one embodiment, an adenoviral vector may be employed, thereby providing for transient expression. In another embodiment, an adeno-associated viral vector or a lentiviral vector may be employed, thereby resulting in stable expression. For $I_{Kur}$ modification, systemic delivery of a genetic inhibitor may be employed due to the specificity of $I_{Kur}$ in the atria. The vectors may also be delivered locally, e.g., the vectors may be delivered by a biocompatible material forming a patch or scaffold (e.g., formed from extracellular matrix, ECM) that is placed in or on the atria. The vectors may then be transferred to target tissue by electrophoresis or photolysis of a caged vector.

The vector may include tissue-specific transcription control elements, for instance, a cardiac-specific or atrial-specific promoter, and so may be delivered systemically. In one embodiment, the vector may include a constitutive promoter (e.g., CMV). In one embodiment, the vector may include an inducible promoter such as one responsive to a stimulus such as electromagnetic energy, light or a drug, which stimulus may be delivered via an interventional cardiology device. In one embodiment, genetic inhibitors are expressed by an inducible promoter responsive to a stimulus like electromagnetic energy, light, a drug or a rapid electrical rhythm in the atria. In one embodiment, the therapy is based on rhythm detected, i.e., a sensed SR rhythm provides for a preventive gene expression response, and a sensed AF rhythm provides for a conversion gene expression response. Thus, in one embodiment, the invention provides a system that can detect atrial state. In one embodiment, the invention provides for system in which a controlling signal elicits a desired gene expression response.

In one embodiment, genetic inhibition of $I_{Kur}$ (Kv1.5) prolongs ERP to terminate or prevent AF. In another embodiment, expression of Cx40 improves cell-cell coupling to eliminate an AF substrate. Because Kv1.5, $I_{Kur}$ and Cx40 are preferentially expressed in human atria, altering their expression provides for a target for AF therapy that has high specificity. Moreover, the use of device- or drug-based stimulation to control AF gene expression therapy may provide for further specificity. In one embodiment, the devices and systems of the invention may include components for automatic AF detection, as well as for activating gene expression and optionally decreasing gene expression, thus allowing for spatial and temporal control of the therapy.

DETAILED DESCRIPTION OF THE INVENTION

Definitions

Figure 1:
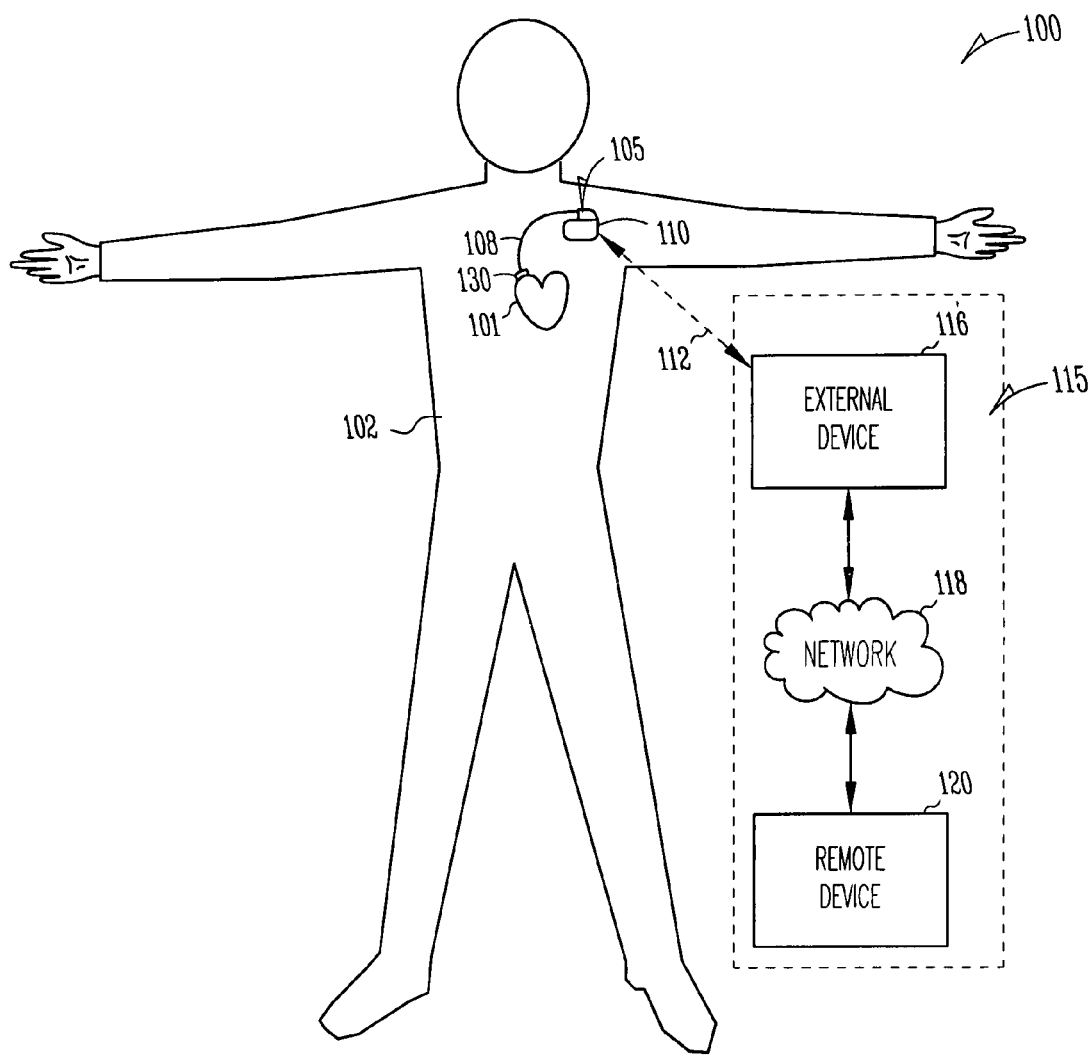
FIG. 1 is an illustration of an embodiment of a biologic therapy system and portions of an environment in which the system is used.

By "nucleic acid", "oligonucleotide", and "polynucleotide" or grammatical equivalents herein means at least two nucleotides covalently linked together.

"Recombinant," as applied to a polynucleotide, means that the polynucleotide is the product of various combinations of cloning, restriction and/or ligation steps, and other procedures that result in a construct that is distinct from a polynucleotide found in nature. Recombinant as applied to a protein means that the protein is the product of expression of a recombinant polynucleotide.

"In vivo" gene/protein delivery, gene/protein transfer, gene/protein therapy and the like as used herein, are terms referring to the introduction of an exogenous (isolated) polynucleotide or protein directly into the body of an organism, such as a human or non-human mammal, whereby the exogenous polynucleotide or protein is introduced to a cell of such organism in vivo.

The term "corresponds to" is used herein to mean that a polynucleotide or protein sequence is homologous (i.e., may be similar or identical, not strictly evolutionarily related) to all or a portion of a reference polynucleotide or protein sequence. In contradistinction, the term "complementary to" is used herein to mean that the complementary polynucleotide sequence is able to hybridize to the other strand. As outlined below, preferably, the homology between the two sequences is at least 70%, preferably 85%, and more preferably 95%, identical.

The terms "substantially corresponds to" or "substantial identity" or "homologous" as used herein denotes a characteristic of a nucleic acid or protein sequence, wherein a nucleic acid or protein sequence has at least about 70% sequence identity as compared to a reference sequence, typically at least about 85% sequence identity, and preferably at least about 95% sequence identity, as compared to a reference sequence. The reference sequence may be a subset of a larger sequence, such as a portion of a gene or flanking sequence, or portion of protein. However, the reference sequence is at least 20 nucleotides long, typically at least about 30 nucleotides long, and preferably at least about 50 to 100 nucleotides long, or, for peptides or polypeptides, at least 7 amino acids long, typically at least 10 amino acids long, and preferably at least 20 to 30 amino acids long. "Substantially complementary" as used herein refers to a nucleotide sequence that is complementary to a sequence that substantially corresponds to a reference sequence.

"Specific hybridization" is defined herein as the formation of hybrids between a polynucleotide which may include substitutions, deletion, and/or additions as compared to a reference sequence and a selected target nucleic acid sequence, wherein the polynucleotide preferentially hybridizes to a target nucleic acid sequence such that, for example, at least one discrete band can be identified on a Northern or Southern blot of DNA prepared from cells that contain the target nucleic acid sequence. It is evident that optimal hybridization conditions will vary depending upon the sequence composition and length(s) of the polynucleotide(s) and target(s), and the experimental method selected by the practitioner. Various guidelines may be used to select appropriate hybridization conditions.

"Treatment" or "therapy" as used herein refers to administering, to an individual patient, agents that are capable of eliciting a prophylactic, curative or other beneficial effect in the individual.

"Gene therapy" as used herein refers to administering, to an individual patient, vectors comprising a gene encoding a beneficial gene product.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamivirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA,* 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

A "disease allele" refers to an allele of a gene that is capable of producing a recognizable disease. However, not all conditions or populations having a certain condition have a known disease allele. A disease allele may be dominant or recessive and may produce disease directly or when present in combination with a specific genetic background or pre-existing pathological condition. A disease allele may be present in the gene pool (an inherited disease allele) or may be generated de novo in an individual by somatic mutation (an acquired disease allele).

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

The term "transduction" denotes the delivery of a polynucleotide to a recipient cell either in vivo or in vitro, via a viral vector, e.g., via a replication-defective viral vector, such as via a recombinant adenovirus or AAV.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA, and portions of both double stranded or single stranded sequence. The polynucleotide may be DNA, both genomic and cDNA, RNA or a hybrid, where the polynucleotide contains any combination of deoxyribo- and ribo-nucleotides, and any combination of bases, including uracil, adenine, thymine, cytosine, guanine, inosine, xathanine and hypoxathanine, etc. Thus, for example, chimeric DNA-RNA molecules may be used such as described in Cole-Strauss et al., *Science,* 273:1386 (1996) and Yoon et al., *Proc. Natl. Acad. Sci. USA,* 93:2071 (1996). It also includes modified polynucleotides such as methylated and/or capped polynucleotides.

A "gene," "polynucleotide," "coding region," or "sequence" which "encodes" a particular gene product, is a nucleic acid molecule which is transcribed and optionally also translated into a gene product, e.g., an antisense sequence or a polypeptide, in vitro or in vivo when placed under the control of appropriate regulatory sequences. The "coding" region may be present in either a cDNA, genomic DNA, RNA form, or a hybrid. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

By "cardiac-specific enhancer or promoter" is meant an element, which, when operably linked to a promoter or alone, respectively, directs gene expression in a cardiac cell and does not direct gene expression in all tissues or all cell types. Cardiac-specific enhancers or promoters may be naturally occurring or non-naturally occurring. One skilled in the art will recognize that the synthesis of non-naturally occurring enhancers or promoters can be performed using standard oligonucleotide synthesis techniques.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a signal or targeting peptide sequence is operably linked to another protein if the resulting fusion is secreted from a cell as a result of the presence of a secretory signal peptide or into an organelle as a result of the presence of an organelle targeting peptide.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

"Gene regulation" or "Gene regulatory therapy" as used herein includes delivery of one or more gene regulatory signals to regulate gene expression in a gene therapy vector. The gene regulatory signals include signals that trigger a transcriptional control element, e.g., a promoter.

General Overview

This document describes, among other things, methods, devices and systems for the control of AF gene therapy. In one embodiment, a mammal having or at risk of having AF is subjected to gene therapy which is intended to inhibit, prevent or treat AF. The gene therapy vector encodes at least one gene product that is operably linked to at least one transcriptional control element, forming an expression cassette. In one embodiment, the gene therapy vector includes at least one transgene that encodes a gene product corresponding to a membrane bound protein, e.g., a gap junction or an ion channel protein, including an antisense sequence, for instance, an antisense oligonucleotide or siRNA. Thus, the expression of the gene product is under the control of a transcriptional control element, such as a regulatable promoter, e.g., an inducible promoter, or an enhancer. For instance, the enhancer may be a glucocorticoid responsive enhancer or the promoter may be an electromagnetic responsive promoter. In one embodiment, the expression of the gene is also tissue-specific, e.g., cardiac cell-specific, due to a tissue-specific promoter and/or enhancer. For instance, the enhancer may be a muscle creatine kinase (mck) enhancer, or the promoter may be an alpha-myosin heavy chain (MyHC) or beta-MyHC promoter (see Palermo et al., Circ. Res., 78, 504 (1996)). To treat AF, a vector of the invention may include a transcriptional regulatory element from a gene that is upregulated in patients having AF, e.g., genes associated with the production of reactive oxygen species (ROS) including flavin containing monooxygenase I, monoamine oxidase B, ubiquitin specific protease 8, tyrosinase-related protein 1, tyrosine 3 related monoxygenase, MMP-2 or MMP-7. Optionally, a combination of gene therapy vectors, each with a different transgene and in one embodiment at least one of which includes a regulatable transcriptional control element, is employed.

In comparison to current, less than optimal therapies for AF, the present invention provides for genetic intervention. Genetic intervention is advantageous because relevant genes may be specifically targeted to the atria, gene expression thereof may be physiologically responsive and/or regulatable with specific transcriptional control elements, it is less invasive and has reduced surgical complications, and/or it may be therapeutic as well as preventive. The targets for AF are several ion channels that determine the action potential duration (APD) and the effective refractory period (ERP). In one embodiment, the targets are potassium channels associated with $I_{Kur}$, $I_{K1}$, or $I_f$, or gap junctions, e.g., gap junctions (Cx 40, 43, 45) that are expressed in cells so that an impulse is propagated. The control of those genes in atria may result in prevention, suppression, and/or termination via restoration (or prolongation) of normal APD and ERP.

In one embodiment, the invention provides methods, devices and systems for suppressing pathologically upregulated $I_{K1}$ in atria, so as to restore normal or prolong APD and ERP, thereby inhibiting the occurrence of AF, especially of the re-entry type. In one embodiment, the invention provides methods, devices and systems for suppressing $I_{Kur}$, thereby prolonging APD without affecting the heart rate and the integrity of the normal electrophysiology. In one embodiment, the invention provides a genetic therapy for AF, in which a genetic inhibitor of $I_{Kur}$, e.g., a vector which expresses a dominant negative, siRNA, or antisense RNA, inhibits $I_{Kur}$, thereby modulating afflicted (or susceptible) AF substrates. In one embodiment, genetic inhibitors of $I_{Kur}$ are delivered and their expression/activation controlled by interventional cardiology devices. In one embodiment, since $I_{Kur}$ is only present in atria, systemic delivery of the genetic inhibitor is envisioned. In one embodiment, the genetic inhibitor may have a cardiac-specific promoter, and the inhibitor is systemically delivered. In one embodiment, because gap junctions are responsible for the intercellular transfer of electrical current, and defects in gap junctions may impair conduction and thereby promote AF, the invention provides methods, devices and systems which express recombinant wild-type proteins that form gap junctions, thus providing treatment for AF.

In one embodiment, the nucleotide sequences are specific for the hyperpolarization-activated cation channel gene (HCN) or a portion thereof. One or more isoforms of HCN may be used in the methods of the invention. Four isoforms of the HCN family, HCN1, HCN2, HCN3, and HCN4 have been identified. The HCN4 isoform may be the predominant subunit encoding for the cardiac funny current channel in the SA node, whereas the HCN2 isoform is in the ventricle and various ratios of HCN1, HCN2 and HCN4 isoforms are in the atria and conduction system, e.g., Purkinje fiber.

A variety of dominant negative proteins can be prepared for use in the methods of the invention. For example, ion channel proteins are recognized as one protein family for which dominant negative proteins can be readily made, e.g., by removing selected transmembrane domains. In most cases, the function of the ion channel binding complex is substantially reduced or eliminated by interaction of a dominant negative ion channel protein. For example, a DNA encoding a protein comprising one or more transmembrane domains is modified so that at least 1 and preferably 2, 3, 4, 5, 6 or more of the transmembrane domains are eliminated. The resulting modified protein may form a binding complex with at least one other protein and inhibit normal function of the binding complex, e.g., as assayed by standard ligand binding assays or electrophysiological assays. A dominant negative protein may exhibit at least 10 percent or greater inhibition of the activity of the binding complex; more preferably at least 20 percent or greater; and still more preferably at least about 30, 40, 50, 60, 70, 80, or 100 percent or greater inhibition of the binding complex activity relative to the full-length protein.

In another embodiment, a cDNA encoding a desired protein for use in the present methods can be modified so that at least one amino acid of the protein is deleted or substituted by a conservative or non-conservative amino acid. For example, a tyrosine amino acid substituted with a phenylalanine would be an example of a conservative amino acid substitution, whereas an arginine replaced with an alanine would represent a non-conservative amino acid substitution.

In another embodiment, a siRNA approach is employed. For instance, target sequences of 21 nucleotides that are located within a region of the coding sequence that is within 50-100 nucleotides of start codon and within 50-100 nucleotides from the termination codon are selected. The presence of AA at the start sequence allows for the use of dTdT at the 3' end of the antisense sequence. The sense strand can be synthesized with dTdT at the 3' end, because only the antisense strand is involved in target recognition. Moreover, the use of dTdT makes the siRNA duplex more resistant to exonucleic activity. The G-C content of a particular sequence may also be used for selecting target sequences. The content may be less than 50%, e.g., in the 40% range, although successful gene silencing has been reported with siRNA having between 50 and 60% G-C content. Sequences with repeats of three or more G's or C's are generally avoided, as their presence may initiate molecular secondary structures preventing effective siRNA silencing hybridization. Stretches of A's and T's may also be avoided. Target sequences that have more than 15 contiguous nucleotide sequence identity to other known genes are avoided.

In one embodiment, concurrent with or after gene therapy, a device which is capable regulating expression of the gene(s) in the gene therapy vector is provided to the mammal. In response to detection of a symptom of AF, e.g., a change in a physiological parameter indicative of fibrillation, the device emits a signal which activates a regulatable transcriptional control element in the gene therapy vector. Such signals include, but are not limited to, an electric field, electromagnetic field, light, and/or chemical agents such as a biologic agent (i.e., one encoded by DNA) or a nonbiologic agent, e.g., a beta adrenergic blocker, an alpha adrenergic blocker, a calcium channel blocker, an ACE inhibitor or an angiotensin II blocker. In one embodiment, after expression from the gene therapy vector is induced and a desirable change in the physiological parameter detected, the signal is discontinued. In another embodiment, the signal is emitted for a predetermined time period. Thus, gene expression may be turned on and off or titrated by controlling signals emitted by the device.

The present invention also provides a system to deliver one or more vectors, in a spatially controlled manner to cells or tissue of a mammal. In one embodiment, to prevent, inhibit or treat AF in a mammal, a biocompatible material having the vector, e.g., a polymer matrix having the vector is applied to the atria of the mammal. Thus, delivery of the vector, which is embedded or applied to a polymer matrix, to the atria provides for localized delivery, optionally at a lower dosage relative to systemic delivery. In one embodiment, the vector in the polymer matrix encodes a dominant negative gene product. In one embodiment, the vector in the polymer matrix includes a gene or a portion thereof for expressing antisense sequence, which in turn can inhibit gene expression, mainly by binding to messenger RNA of the target gene, and thus have the ability to block the expression of endogenous gene products.

Polymer Matrix

The polymer matrix may be formed of any physiologically compatible material which generally retains the vector (which is a charged molecule) or optionally other agents including other agents under physiological conditions for a sustained period of time, e.g., for months or years. The polymer matrix may extrude (release) the vector in response to an electric field created by an electrical signal or the matrix may provide for passive delivery. The electric signal may be generated in response to the detection of a physiological signal, e.g., such as associated with AF.

The vector or optional other agent(s) may be introduced to a solution of monomers prior to polymerization or to the polymer matrix, e.g., dissolved in a solvent (e.g., water, propylene, glycol, etc.) and the resulting solution can be incorporated into the polymer matrix material. Once the vector is embedded in or applied to a polymer matrix, the resulting delivery device may be coupled to an implantable pulse generator. Upon delivery of an electric field, the vector or optional other agent(s) is released from the matrix at a rate which is greater than the rate of release in the absence of the electric field. In particular, the vector in the delivery device is released to adjacent cells or tissue or the vessel lumen in response to an electric field generated by, for instance, an implantable pulse generator, which release is in an amount proportional to the applied electric field. Once the electric signal is stopped, the vector is no longer released or released at a rate which is significantly reduced relative to the rate of release in the presence of the electric field. Thus, the delivery of the vectors may be spatially and/or temporally controlled by the placement of the device and optionally by active release of the vector, e.g., by the device.

The matrix materials will preferably be physiologically inert and capable of retaining the charged molecule to be delivered. Matrix materials which may be used include: polyacetic or polyglycolic acid and derivatives thereof, polyorthoesters, polyesters, polyurethanes, polyamino acids such as polylysine, lactic/glycolic acid copolymers, polyanhydrides and ion exchange resins such as sulfonated polytetrafluorethylene, or combinations thereof. Biocompatible materials may thus include polyglycolic acid and derivatives thereof, carboxyl containing polymers, polyorthoesters, polyesters, e.g., hydroxyl containing polyesters, polyurethanes, polyamino acids such as polylysine, lactic/glycolic acid copolymers, polyanhydrides and ion exchange resins such as sulfonated polytetrafluorethylene, polydimethyl siloxanes (silicone rubber) or combinations thereof. Reactive groups on the polymers, for example, hydroxy or amino groups, can be acetylated (e.g., polymer-O—C(=O)CH$_3$ or polymer-NR—C(=O)CH$_3$), and those groups can be prepared either before or after polymerization of monomers.

Additionally, the biocompatible material may be formed from natural proteins or materials which optionally may be modified, e.g., crosslinked using a crosslinking agent such as 1-ethyl-3-(3-dimethylamino-propyl)carbodiimide hydrochloride. Such natural materials include polysaccharides, e.g., cellulose including regenerated cellulose (rayon), albumin, collagen, fibrin, alginate, extracellular matrix (ECM), e.g., xenogeneic ECM, hyaluronan, chitosan, gelatin, keratin, potato starch hydrolyzed for use in electrophoresis, and agar-agar (agarose), or other "isolated materials". An "isolated" material has been separated from at least one contaminant structure with which it is normally associated in its natural state such as in an organism or in an in vitro cultured cell population.

In one embodiment, the material may include liposomes, a hydrogel, cyclodextrins, nanocapsules or microspheres. Thus, a biocompatible material includes synthetic polymers in the form of hydrogels or other porous materials, e.g., permeable configurations or morphologies, such as polyvinyl alcohol, polyvinylpyrrolidone and polyacrylamide, polyethylene oxide, poly(2-hydroxyethyl methacrylate); natural polymers such as gums and starches; synthetic elastomers such as silicone rubber, polyurethane rubber; and natural rubbers, and include poly[α(4-aminobutyl)]-1-glycolic acid, polyethylene oxide (Roy et al., *Mol. Ther.,* 7:401 (2003)), poly orthoesters (Heller et al., *Adv. Drug Delivery Rev.,* 54:1015 (2002)), silk-elastin-like polymers (Megeld et al., *Pharma. Res.,* 19:954 (2002)), alginate (Wee et al., *Adv. Drug Deliv. Rev.,* 31:267 (1998)), EVAc (poly(ethylene-co-vinyl acetate), microspheres such as poly(D,L-lactide-co-glycolide) copolymer and poly (L-lactide) and poly glycolide, polydioxenone, poly(N-isopropylacrylamide)-b-poly(D,L-lactide), a soy matrix such as one cross-linked with glyoxal and reinforced with a bioactive filler, e.g., hydroxylapatite, poly(epsilon-caprolactone)-poly(ethylene glycol) copolymers, poly (acryloyl hydroxyethyl) starch, polylysine-polyethylene glycol, an agarose hydrogel, or a lipid microtubule-hydrogel.

In one embodiment, the vector is encapsulated by, embedded in or applied to a biocompatible material, e.g., a nonbiodegradable or biodegradable material, respectively, including but not limited to hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols.

In some embodiments, the vector is embedded in or encapsulated by a biocompatible and optionally biodegradable polymeric such as collagen, fibrin, polyhydroxyalkanoates, cellulose, polylactic-polyglycolic acid, or a polyanhydride.

Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D, L-lactide-co-glycolide) block copolymers, polyglycolide, polylactides (PLLA or PDLA), poly(caprolactone) (PCL), poly(dioxanone) (PPS) or cellulose derivatives such as cellulose acetate. In an alternative embodiment, a biologically derived polymer, such as protein, collagen, e.g., hydroxylated collagen, or fibrin, or polylactic-polyglycolic acid or a polyanhydride, is a suitable polymeric matrix material.

In another embodiment, the biocompatible material includes polyethyleneterephalate, polytetrafluoroethylene, copolymer of polyethylene oxide and polypropylene oxide, a combination of polyglycolic acid and polyhydroxyalkanoate, or gelatin, alginate, collagen, hydrogels, poly-3-hydroxybutyrate, poly-4-hydroxybutyrate, and polyhydroxyoctanoate, and polyacrylonitrilepolyvinylchlorides.

The above examples are provided for reference only, and the range of suitable polymer matrix materials should not be construed as limited to those materials listed above. The polymer matrix material can be hydrophilic, hydrophobic, or amphiphilic, provided it meets the physical characteristics described above. See also U.S. Pat. No. 5,087,243 and Avitall et al., *Circ.,* 85:1582 (1992). The polymer matrix preferably stabilizes the vector(s) and other optional agents in the polymer matrix.

A polymer matrix may also be present in a selectively semipermeable membrane such as a dialysis membrane, nylon or polysulfoxy. In one embodiment, the semipermeable membrane is not biodegradable.

Gene Therapy Vectors

Gene therapy vectors include, for example, viral vectors, liposomes and other lipid-containing complexes, and other macromolecular complexes capable of mediating delivery of a gene to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Gene therapy vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene therapy vectors are described below. Gene therapy vectors may be administered via any route including, but not limited to, intramuscular, buccal, rectal, intravenous or intracoronary administration, and transfer to cells may be enhanced using electroporation and/or iontophoresis.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., *Meth. Mol. Med.*, 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfilsion. Adenoviral vectors have been shown to result in transient expression of therapeutic genes in vivo, peaking at 7 days and lasting approximately 4 weeks. The duration of transgene expression may be improved in systems utilizing cardiac specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., *Nat. Med.*, 8:864 (2002); Lynch et al., *Circ. Res.*, 80:197 (1997)).

Herpesvirus/Amplicon

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particularly useful for delivery of large genes, e.g., genes encoding ryanodine receptors and titin.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature*, 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Synthetic Oligonucleotides

Antisense oligonucleotides are short (approximately 10 to 30 nucleotides in length), chemically synthesized DNA molecules that are designed to be complementary to the coding sequence of an RNA of interest. These agents may enter cells by diffusion or liposome-mediated transfer and possess relatively high transduction efficiency. These agents are useful to reduce or ablate the expression of a targeted gene while unmodified oligonucleotides have a short half-life in vivo, modified bases, sugars or phosphate groups can increase the half-life of oligonucleotide. For unmodified nucleotides, the efficacy of using such sequences is increased by linking the antisense segment with a specific promoter of interest, e.g., in an adenoviral construct. In one embodiment, electroporation and/or liposomes are employed to deliver plasmid vectors. Synthetic oligonucleotides may be delivered to cells as part of a macromolecular complex, e.g., a liposome, and delivery may be enhanced using techniques such as electroporation.

Regulatable Transcriptional Control Elements

The device of the invention may deliver one or more signals including, but not limited to, light of a particular wavelength or a range of wavelengths, light of a particular energy, acoustic energy, an electric field, a chemical, electromagnetic energy, thermal energy or other forms of temperature or matter, which signal is recognized by a regulatable transcriptional control element in a gene therapy vector.

A variety of strategies have been devised to control in vivo expression of transferred genes and thus alter the pharmacokinetics of in vivo gene transfer vectors in the context of regulatable or inducible promoters. Many of these regulatable promoters use exogenously administered agents to control transgene expression and some use the physiologic milieu to control gene expression. Examples of the exogenous control promoters include the tetracycline-responsive promoter, a chimeric transactivator consisting of the DNA and tetracycline-binding domains from the bacterial tet repressor fused to the transactivation domain of herpes simplex virion protein 16 (Ho et al., *Brain Res. Mol. Brain. Res.*, 41:200 (1996)); a chimeric promoter with multiple cyclic adenosine monophosphate response elements superimposed on a minimal fragment of the 5'-flanking region of the cystic fibrosis transmembrane conductance regulator gene (Suzuki et al., 7:1883 (1996)); the EGR1 radiation-inducible promoter (Hallahan et al., *Nat. Med.*, 1:786 (1995)); and the chimeric GRE promoter (Lee et al., *J. Thoracic Cardio. Surg.*, 118:26 (1996)), with 5 GREs from the rat tyrosine aminotransferase gene in tandem with the insertion of Ad2 major late promoter TATA box-initiation site (Narumi et al., *Blood*, 92:812 (1998)). Examples of the physiologic control of promoters include a chimera of the thymidine kinase promoter and the thyroid hormone and retinoic acid-responsive element responsive to both exogenous and endogenous tri-iodothyroniine (Hayashi et al., *J. Biol. Chem.*, 269:23872 (1994)); complement factor 3 and serum amyloid A3 promoters responsive to inflammatory stimuli; the grp78 and BiP stress-inducible promoter, a glucose-regulated protein that is inducible through glucose deprivation, chronic anoxia, and acidic pH (Gazit et al., *Cancer Res.*, 55:1660 (1995)); and hypoxia-inducible factor 1 and a heterodimeric basic helix-loop-helix protein that activates transcription of the human erythropoietin gene in hypoxic cells, which has been shown to act as a regulatable promoter in the context of gene therapy in vivo (Forsythe et al., *Mol. Cell Biol.*, 16:4604 (1996)).

Regulatable transcriptional elements useful in gene therapy vectors and methods of the invention include, but are not limited to, a truncated ligand binding domain of a progesterin receptor (controlled by antiprogestin), a tet promoter (controlled by tet and dox) (Dhawan et al., *Somat. Cell. Mol. Genet.*, 21, 233 (1995); Gossen et al., *Science*, 268:1766 (1995); Gossen et al., *Science*, 89:5547 (1992); Shockett et al., *Proc. Natl. Acad. Sci. USA*, 92, 6522 (1995)), hypoxia-inducible nuclear factors (Semenza et al., *Proc. Natl. Acad. Sci. USA*, 88, 5680 (1991); Semenza et al., *J. Biol. Chem.*, 269, 23757)), steroid-inducible elements and promoters, such as the glucocorticoid response element (GRE) (Mader and White, *Proc. Natl. Acad. Sci. USA*, 90, 5603 (1993)), and the fusion consensus element for RU486 induction (Wang et al., *Proc. Natl. Acad. Sci. USA*, 91:818 (1994)), those sensitive to electromagnetic fields, e.g., those present in metallothionein I or II, c-myc, and HSP70 promoters (Lin et al., *J. Cell. Biochem.*, 81:143 (2001); Lin et al., *J. Cell. Biochem.*, 54:281 (1994); U.S. published application 20020099026)), and electric pulses (Rubenstrunk et al., *J. Gene Med.*, 5:773 (2003)), as well as a yeast GAL4/TATA promoter, auxin inducible element, an ecdysone responsive element (No et al., *Proc. Natl. Acad. Sci. USA*, 93:3346 (1996)), an element inducible by rapamycin (FK506) or an analog thereof (Rivera et al., *Nat. Med.*, 2:1028 (1996); Ye et al., *Science*, 283:88 (1999); Rivera et al., *Proc. Natl. Acad. Sci. USA*, 96:8657 (1999)), a tat responsive element, a metal, e.g., zinc, inducible element, a radiation inducible element, e.g., ionizing radiation has been used as the inducer of the promoter of the early growth response gene (Erg-1) (Hallahan et al., *Nat. Med.*, 1:786 (1995)), an element which binds nuclear receptor PPARγ (peroxisome proliferators activated receptors), which is composed of a minimal promoter fused to PPRE (PPAR responsive elements, see WO 00/78986), a cytochrome P450/A1 promoter, a MDR-1 promoter, a promoter induced by specific cytokines (Varley et al., *Nat. Biotech.*, 15:1002 (1997)), a light inducible element (Shimizu-Sato et al., *Nat. Biotech.*, 20:1041 (2002)), a lacZ promoter, and a yeast Leu3 promoter.

In some embodiments, cell- or tissue-specific control elements, such as muscle-specific and inducible promoters, enhancers and the like, will be of particular use, e.g., in conjunction with regulatable transcriptional control elements. Such control elements include, but are not limited to, those derived from the actin and myosin gene families, such as from the myoD gene family (Weintraub et al., *Science*, 251, 761 (1991)); the myocyte-specific enhancer binding factor MEF-2 (Cserjesi and Olson, *Mol. Cell Biol.*, 11, 4854 (1991)); control elements derived from the human skeletal actin gene (Muscat et al., *Mol. Cell Bio.*, 7, 4089 (1987)) and the cardiac actin gene; muscle creatine kinase sequence elements (Johnson et al., *Mol. Cell Biol.*, 9, 3393 (1989)) and the murine creatine kinase enhancer (mCK) element; control elements derived from the skeletal fast-twitch troponin C gene, the slow-twitch cardiac troponin C gene and the slow-twitch troponin I genes.

Cardiac cell restricted promoters include but are not limited to promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

In other embodiments, disease-specific control elements may be employed. Thus, control elements from genes associated with a particular disease, including but not limited to any of the genes disclosed herein may be employed in vectors of the invention.

Nevertheless, other promoters and/or enhancers which are not specific for cardiac cells or muscle cells, e.g., RSV promoter, may be employed in the expression cassettes and methods of the invention. Other sources for promoters and/or enhancers are promoters and enhancers from the Csx/NKX 2.5 gene, titin gene, α-actinin gene, myomesin gene, M protein gene, cardiac troponin T gene, RyR2 gene, Cx40 gene, and Cx43 gene, as well as genes which bind Mef2, dHAND, GATA, CarG, E-box, Csx/NKX 2.5, or TGF-beta, or a combination thereof.

The response of the regulatable transcriptional control element to one or more intermittent signals, a prolonged signal or different levels of a signal, may be tested in vitro or in vivo. The vector may include the regulatable transcriptional control element linked to a marker gene, i.e., one which is readily detectable or capable of detection such as green fluorescent protein (GFP). For example, a vector having a promoter which is sensitive to electrical pulses, a MT-I or MT-II promoter (Rubenstruck et al., *J. Gene Med.*, 5:773 (2003)), is linked to an open reading frame for a marker gene. The resulting expression cassette, e.g., one which is introduced to an adenovirus vector or to a plasmid vector, is employed to infect or transfect murine cells, e.g., murine cardiac cells, or heart sections. An electrode system designed for use in a small flask is used to deliver electrical pulses. Then fluorescence in the cells or a lysate thereof is detected, and/or or vector specific RNA is measured, for instance, using RT-PCR, and optionally compared to data from control cells. Similarly, a vector having a promoter which is sensitive to electrical pulses is linked to an open reading frame for a therapeutic gene, e.g., Serca2, introduced to cells, e.g., cardiac cells such as those with decreased levels of the gene product encoded by the therapeutic gene, and the phenotype of the recombinant cells compared to control cells. Vectors may also be introduced to a non-human large animal model, e.g., pigs, to determine the level and spatial expression of the exogenously introduced gene in response to signals, e.g., electrical pulses, from an implantable device in that animal.

Vector or Recombinant Cell Delivery

Several techniques have been developed for cardiac gene delivery, including pericardial infusion, endomyocarial injection, intracoronary injection, coronary venous retroperfusion, and aortic root injection (Isner, *Nature*, 415:234 (2002)). The different techniques achieve variable response in homogeneity of gene delivery, resulting in focal gene expression within the heart (Hajjar et al., *Circ. Res.*, 86:616 (2000). For this reason, techniques that achieve diffuse uptake would seem to be superior. Two such methods utilize the heart's arterial and venous circulation to accomplish disseminated viral transfection. Arterial injection, performed directly through a percutaneous approach or indirectly by an infusion into the cross-clamped aorta, has shown promise in animal models of heart failure and is appealing in that it can be performed either at the time of cardiac surgery or as percutaneous intervention (Hajjar et al., *PNAS USA*, 95:5251 (1998)). Similarly, retroperfusion through the coronary sinus appears to produce a more global gene expression in comparison with techniques of localized or focal injection (Boeckstegers et al., *Circ.*, 100:1 (1999)).

Recombinant cells may be administered intravenously, transvenously, intramyocardially or by any other convenient route, and delivered by a needle, catheter, e.g., a catheter which includes an injection needle or infusion port, or other suitable device.

Direct Myocardial Injection

Direct myocardial injection of plasmid DNA as well as virus vectors, e.g., adenoviral vectors, and cells including recombinant cells has been documented in a number of in vivo studies. This technique when employed with plasmid DNA or adenoviral vectors has been shown to result in effective transduction of cardiac myocytes. Thus, direct injection may be employed as an adjunct therapy in patients undergoing open-heart surgery or as a stand-alone procedure via a modified thorascope through a small incision. In one embodiment, this mode of administration is used to deliver a gene or gene product that would only require limited transfection efficiency to produce a significant therapeutic response, such as a gene that encodes for or leads to a secreted product (e.g., VEGF, endothelial nitric oxide synthase). Virus, e.g., pseudotyped, or DNA- or virus-liposome complexes may be delivered intramyocardially.

Catheter-Based Delivery

Intracoronary delivery of genetic material can result in transduction of approximately 30% of the myocytes predominantly in the distribution of the coronary artery. Parameters influencing the delivery of vectors via intracoronary perfusion and enhancing the proportion of myocardium transduced include a high coronary flow rate, longer exposure time, vector concentration, and temperature. Gene delivery to a substantially greater percent of the myocardium may be enhanced by administering the gene in a low-calcium, high-serotonin mixture (Donahue et al., *Nat. Med.*, 6:1395 (2000)). The potential use of this approach for gene therapy for heart failure may be increased by the use of specific proteins that enhance myocardial uptake of vectors (e.g., cardiac troponin T).

Improved methods of catheter-based gene delivery have been able to achieve almost complete transfection of the myocardium in vivo. Hajjar et al. (*Proc. Natl. Acad. Sci. USA*, 95:5251 (1998)) used a technique combining surgical catheter insertion through the left ventricular apex and across the aortic valve with perfusion of the gene of interest during cross-clamping of the aorta and pulmonary artery. This technique resulted in almost complete transduction of the heart and could serve as a protocol for the delivery of adjunctive gene therapy during open-heart surgery when the aorta can be cross-clamped.

Recombinant cells may also be delivered via catheter.

Pericardial Delivery

Gene delivery to the ventricular myocardium by injection of genetic material into the pericardium has shown efficient gene delivery to the epicardial layers of the myocardium. However, hyaluronidase and collagenase may enhance transduction without any detrimental effects on ventricular function. Recombinant cells may also be delivered pericardially.

Intravenous Delivery

Intravenous gene delivery may be efficacious for myocardial gene delivery. However, to improve targeted delivery and transduction efficiency of intravenously administered vectors, targeted vectors may be employed. In one embodiment, intravenous administration of DNA-liposome or antibody-DNA complexes may be employed.

Lead-Based Delivery

Gene delivery can be performed by incorporating a gene delivery device or lumen into a lead such as a pacing lead, defibrillation lead, or pacing-defibrillation lead. An endocardial lead including a gene delivery device or lumen allows gene delivery to the endocardial layers of the myocardium. An epicardial lead including a gene delivery device or lumen allows gene delivery to the endocardial layers of the myocardium. A transvenous lead including a gene delivery device or lumen may also allow intravenous gene delivery. Lead-based delivery is particularly advantageous when the lead is used to deliver electrical and gene therapies to the same region.

Generally any route of administration may be employed, including oral, mucosal, intramuscular, buccal and rectal administration. For certain vectors, certain route of administration may be preferred. For instance, viruses, e.g., pseudotyped virus, and DNA- or virus-liposome, e.g., HVJ-liposome, may be administered by coronary infusion, while HVJ-liposome complexes may be delivered pericardially.

Recombinant cells may also be delivered systemically, e.g., intravenously.

Dosages and Dosage Forms

The amount of gene therapy vector(s), e.g., those which are present in a recombinant cell or in acellular form, administered and device based signal emitted to achieve a particular outcome will vary depending on various factors including, but not limited to, the gene and promoter chosen, the condition, patient specific parameters, e.g., height, weight and age, and whether prevention or treatment is to be achieved. The gene therapy vector/device system of the invention is amenable to chronic use for prophylactic purposes.

Vectors of the invention may conveniently be provided in the form of formulations suitable for administration, e.g., into the blood stream (e.g., in an intracoronary artery). A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. Vectors of the present invention should preferably be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors can be provided in a dosage form containing an amount of a vector effective in one or multiple doses. For viral vectors, the effective dose may be in the range of at least about $10^7$ viral particles, preferably about $10^9$ viral particles, and more preferably about $10^{11}$ viral particles. The number of viral particles may, but preferably does not exceed $10^{14}$. As noted, the exact dose to be administered is determined by the attending clinician, but is preferably in 1 ml phosphate buffered saline. For delivery of recombinant cells, the number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered.

In one embodiment, in the case of heart disease, administration may be by intracoronary injection to one or both coronary arteries (or to one or more saphenous vein or internal mammary artery grafts or other conduits) using an appropriate coronary catheter. A variety of catheters and delivery routes can be used to achieve intracoronary delivery, as is known in the art. For example, a variety of general purpose catheters, as well as modified catheters, suitable for use in the present invention are available from commercial suppliers. Also, where delivery to the myocardium is achieved by injection directly into a coronary artery, a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., above, including: Topol, (ed.), *The Textbook of Interventional Cardiology*, 4th Ed. (Elsevier 2002); Rutherford, *Vascular Surgery*, 5th Ed. (W.B. Saunders Co. 2000); Wyngaarden et al. (eds.), *The Cecil Textbook of Medicine*, 22nd Ed. (W.B. Saunders, 2001); and Sabiston, *The Textbook of Surgery*, 16th Ed. (Elsevier 2000)).

By way of illustration, liposomes and other lipid-containing gene delivery complexes can be used to deliver one or more transgenes. The principles of the preparation and use of such complexes for gene delivery have been described in the art (see, e.g., Ledley, *Human Gene Therapy*, 6:1129 (1995); Miller et al., *FASEB Journal*, 9:190 (1995); Chonn et al., *Curr. Opin. Biotech.*, 6:698 (1995); Schofield et al., *British Med. Bull.*, 51:56 (1995); Brigham et al., *J. Liposome Res.*, 3:31 (1993)).

Administration of the gene therapy vector in accordance with the present invention may be continuous or intermittent, depending, for example, upon the recipient's physiological condition, whether the purpose of the administration is therapeutic or prophylactic, and other factors known to skilled practitioners. The administration of the gene therapy vector may be essentially continuous over a preselected period of time or may be in a series of spaced doses. Both local and systemic administration is contemplated.

One or more suitable unit dosage forms comprising the gene therapy vector, which may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

Pharmaceutical formulations containing the gene therapy vector can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions for convenient oral administration or as solutions appropriate for parenteral administration, for instance by intramuscular, subcutaneous or intravenous routes.

The pharmaceutical formulations of the vectors can also take the form of an aqueous or anhydrous solution or dispersion, or alternatively the form of an emulsion or suspension.

Thus, the vector may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

For administration to the upper (nasal) or lower respiratory tract by inhalation, the vector is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the vector may be administered via nose drops, a liquid spray, such as via a plastic bottle atomizer or metered-dose inhaler. Typical of atomizers are the Mistometer (Wintrop) and the Medihaler (Riker).

The local delivery of the vectors can also be by a variety of techniques which administer the vector at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the vectors may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The vector may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents or preservatives.

Devices

Delivering and/or regulating the expression cassette discussed above using an implantable system is discussed below, with reference to FIGS. 1-5. While implantable devices are discussed as a specific example, the present subject matter includes delivering and regulating the expression cassette using one or more of percutaneous, implantable, and external devices.

FIG. 1 is an illustration of an embodiment of a biologic therapy system 100 and portions of an environment in which system 100 is used. System 100 includes an implantable system 105, an external system 115, and a telemetry link 112 providing for communication between implantable system 105 and external system 115. In various embodiments, system 100 is a cardiac rhythm management (CRM) system, or a part of the CRM system, and delivers a biologic therapy to prevent or terminate one or more types of arrhythmia.

Implantable system 105 includes, among other things, implantable medical device 110, a lead system 108, and an implantable biologic therapy device 130. As shown in FIG. 1, implantable medical device 110 is implanted in a body 102. Implantable biologic therapy device 130 delivers one or more therapeutic agents including an expression cassette into body 102 and/or delivers one or more gene regulatory signals suitable for regulating the expression cassette in body 102. In one embodiment, implantable biologic therapy device 130 delivers the one or more therapeutic agents including an expression cassette to a heart 101 of body 102 and/or delivers the one or more gene regulatory signals suitable for regulating the expression cassette already delivered to heart 101. The expression cassette is selected for preventing or terminating the one or more types of arrhythmia and includes any examples of such expression cassette discussed in this document. In one embodiment, implantable medical device 110 includes a biologic therapy controller that controls the delivery of the one or more therapeutic agents and/or the one or more gene regulatory signals from implantable biologic therapy device 130. Lead system 108 provides for access to one or more locations to which the one or more therapeutic agents and/or the one or more gene regulatory signals are delivered. In one embodiment, implantable medical device 110 also includes a pacemaker, a cardioverter/defibrillator, a cardiac resynchronization therapy (CRT) device, a cardiac remodeling control therapy (RCT) device, a drug delivery device or a drug delivery controller, a cell therapy device, or any other implantable medical device. Lead system 108 further includes leads for sensing physiological signals and delivering pacing pulses, cardioversion/defibrillation shocks, and/or pharmaceutical or other substances.

External system 115 includes an external device 116, a network 118, and a remote device 120. External device 116 is within the vicinity of implantable medical device 110 and communicates with implantable medical device 110 bi-directionally via telemetry link 112. Remote device 120 is in a remote location and communicates with external device 116 bi-directionally via network 118, thus allowing a user to monitor and treat a patient from a distant location.

System 100 allows the delivery of the biologic therapy, i.e., delivery of the one or more therapeutic agents and/or the one or more gene regulatory signals, to be triggered by any of implantable medical device 110, external device 116, and remote device 120. In one embodiment, implantable medical device 110 triggers the delivery of the biologic therapy upon detecting a treatable type tachyarrhythmia. In another embodiment, external device 116 or remote device 120 triggers the delivery of the biologic therapy upon detecting an abnormal condition from a signal transmitted from implantable medical device 110. In one specific embodiment, external system 115 includes a processor running a therapy decision algorithm to determine whether and when to trigger the delivery of the biologic therapy. In another specific embodiment, external system 115 includes a user interface to present signals acquired by implantable medical device 110 and/or the detected abnormal condition to a user and receives commands from the user for triggering the delivery of the biologic therapy. In another specific embodiment, the user interface includes a user input incorporated into external device 116 to receive commands from the user and/or the patient treated with system 100. For example, the patient may be instructed to enter a command for the biologic therapy when he senses certain symptoms, and another person near the patient may do the same upon observing the symptoms.

Figure 2:
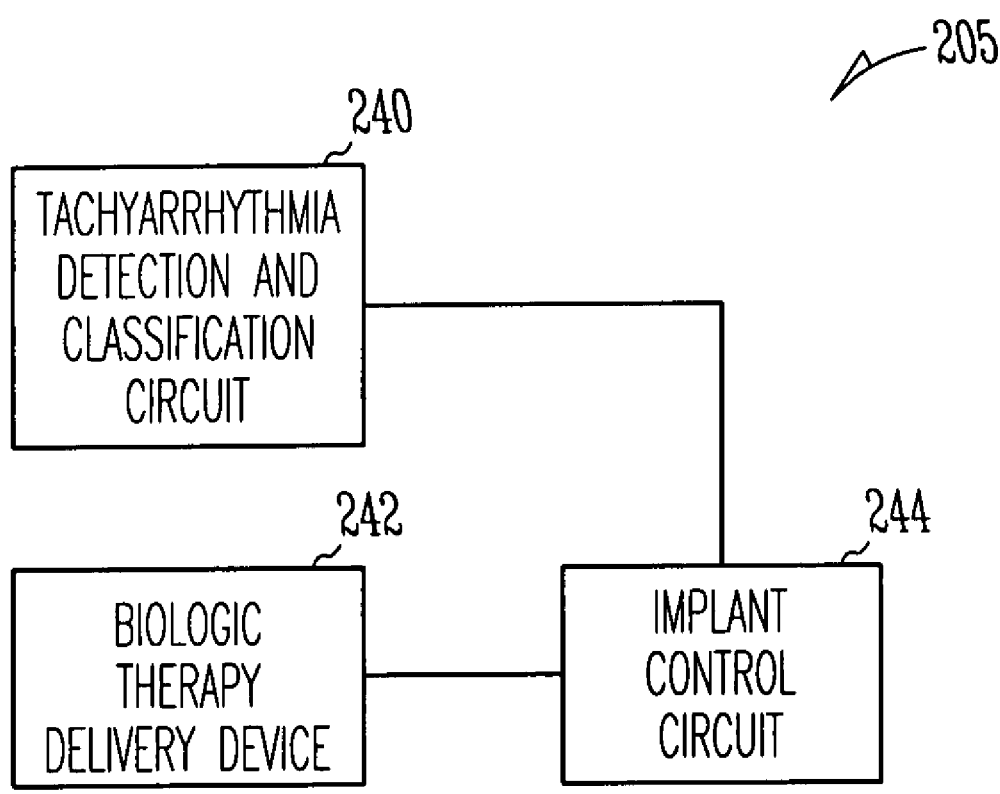
FIG. 2 is a block diagram illustrating an embodiment of an implantable system of the biologic therapy system.

FIG. 2 is a block diagram illustrating an embodiment of an implantable system 205. Implantable system 205 includes a tachyarrhythmia detection and classification circuit 240, a biologic therapy delivery device 242, and an implant control circuit 244. In various embodiments, tachyarrhythmia detection and classification circuit 240, biologic therapy delivery device 242, and implant control circuit 244 are distributed in implantable medical device 110, lead system 108, and implantable biologic therapy device 130.

Tachyarrhythmia detection and classification circuit 240 detects and classifies tachyarrhythmia episodes using one or more intrinsic electrical cardiac signals sensed using lead system 108. In one embodiment, in addition to one or more cardiac signals, tachyarrhythmia detection and classification circuit 240 uses one or more other physiological signals, such as one or more signals indicative of hemodynamic performance, to detect and classify tachyarrhythmia episode. An example of such a tachyarrhythmia detection and classification circuit is discussed in U.S. patent application Ser. No. 11/668,627, entitled "METHOD AND APPARATUS FOR ATRIAL PACING DURING TACHYARRHYTHMIA", filed on Jan. 30, 2007, assigned to Cardiac Pacemakers, Inc., which is incorporated herein by reference in its entirety.

Biologic therapy delivery device 242 delivers the biologic therapy. In various embodiments, biologic therapy delivery device 242 delivers the one or more therapeutic agents and/or the one or more gene regulatory signals. In one example, biologic therapy delivery device 242 delivers the one or more therapeutic agents, including the expression cassette, which does not need to be regulated by the one or more gene regulatory signals after the delivery. In another example, the one or more therapeutic agents including the expression cassette has been administrated using delivery instruments other than implantable system 205, and biologic therapy delivery device 242 delivers the one or more gene regulatory signals to regulate the expression cassette. In another example, biologic therapy delivery device 242 delivers the one or more therapeutic agents, including the expression cassette, and then delivers the one or more gene regulatory signals to regulate the delivered expression cassette.

Implant control circuit 244 controls the delivery of the biologic therapy in response to the detection of a tachyarrhythmia classified as a type to be terminated and/or prevented by the biologic therapy. In one embodiment, the type of tachyarrhythmia to be terminated and/or prevented includes AF. Tachyarrhythmia detection and classification circuit 240 is capable of classifying at least AF. In response to detected tachyarrhythmia classified as AF, implant control circuit 244 initiates a delivery of the biologic therapy including the delivery of the one or more therapeutic agents and/or the one or more gene regulatory signals.

Figure 3:
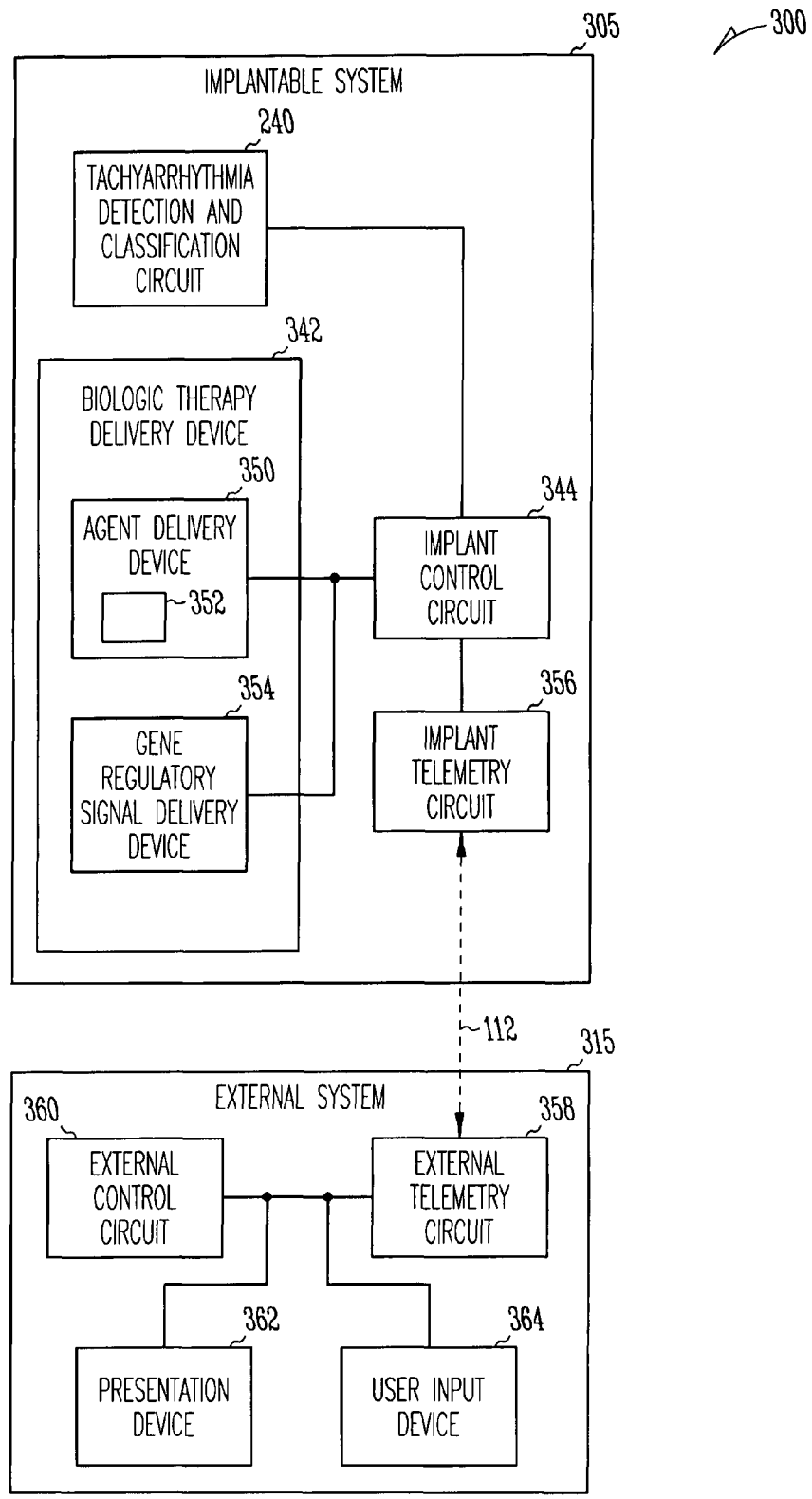
FIG. 3 is a block diagram illustrating an embodiment of the biologic therapy system.

FIG. 3 is a block diagram illustrating an embodiment of a biologic therapy system 300, which represents a specific embodiment of system 100. System 300 includes an implantable system 305, an external system 315, and telemetry link 112 providing for communication between implantable system 305 and external system 315.

Implantable system 305 represents a specific embodiment of implantable system 105 and includes tachyarrhythmia detection and classification circuit 240, a biologic therapy delivery device 342, an implant control circuit 344, and an implant telemetry circuit 356. In the illustrated embodiment, biologic therapy delivery device 342 includes an agent delivery device 350 and a gene regulatory signal delivery device 354. In various embodiments, biologic therapy delivery device 342 includes any one or both of agent delivery device 350 and gene regulatory signal delivery device 354. Agent delivery device 350 contains and delivers one or more agents including an expression cassette 352, which represents any expression cassette discussed in this document. Gene regulatory signal delivery device 354 delivers a gene regulatory signal carrying a form of energy suitable for regulating expression cassette 352 that has been administrated into a target region in a patient's body. Implant control circuit 344 controls the delivery of expression cassette 352 and/or the gene regulatory signal. Implant telemetry circuit 356 receives data from, and transmits data to, external system 315 via telemetry link 112.

Agent delivery device 350 is configured to store expression cassette 352 and release expression cassette 352 when needed. In various embodiments, agent delivery device 350 includes portions of implantable medical device 110, lead system 108, and implantable biologic therapy device 130. In one embodiment, expression cassette 352 is stored in implantable medical device 110 and released via a lumen in lead system 108. In another embodiment, implantable biologic therapy device 130 includes a polymer incorporated into lead system 108. Expression cassette 352 is embedded in the polymer for controlled release. Examples of an agent delivery device are discussed in U.S. patent application Ser. No. 10/645,823, entitled "METHOD AND APPARATUS FOR MODULATING CELLULAR METABOLISM DURING POST-ISCHEMIA OR HEART FAILURE", filed on Aug. 21, 2003 and U.S. patent application Ser. No. 10/890,825, entitled "METHOD AND APPARATUS FOR CONTROLLED GENE OR PROTEIN DELIVERY", filed on Jul. 14, 2004, both assigned to Cardiac Pacemakers, Inc., which are incorporated herein by reference in their entirety.

Gene regulatory signal delivery device 354 delivers the gene regulatory signal that carries a form of energy suitable for regulating expression cassette 352. In various embodiments, expression cassette 352 has been administrated using agent delivery device 350 or another device. Gene regulatory signal delivery device 354 receives a gene regulatory control signal from implant control circuit 344 and, in response, delivers one or more gene regulatory signals in one or more forms of energy being external factors regulating one or more gene expressions. The forms of energy include electrical energy, electromagnetic energy, optical energy, acoustic energy, thermal energy, and any other forms of energy that triggers the gene promoter system. In one embodiment, gene regulatory signal delivery device 354 delivers the one or more gene regulatory signals to the heart. In another embodiment, gene regulatory signal delivery device 354 delivers the one or more gene regulatory signals to the blood. An example of a gene regulatory signal delivery device is discussed in U.S. patent application Ser. No. 10/788,906, entitled "METHOD AND APPARATUS FOR DEVICE CONTROLLED GENE EXPRESSION", filed on Feb. 27, 2004, assigned to Cardiac Pacemakers, Inc., which is incorporated herein by reference in its entirety.

External system 315 includes an external telemetry circuit 358, an external user input device 364, a presentation device 362, and an external control circuit 360. These system components distribute in one or more of external device 116, network 118, and remote device 120, depending on design and medical considerations. External telemetry circuit 358 receives data from, and transmits data to, implantable medical device 110 via telemetry link 112. User input device 364 receives commands and/or parameters from the user and/or the patient to control the delivery of the biologic therapy. Presentation device 362 displays or otherwise presents signals acquired and/or abnormal conditions detected by implantable medical device 110. External control circuit 360 controls the operation of external system 315.

Telemetry link 112 is a wireless bidirectional data transmission link supported by implant telemetry circuit 356 and external telemetry circuit 358. In one embodiment, telemetry link 112 is an inductive couple formed when two coils—one connected to implant telemetry circuit 356 and the other connected to external telemetry circuit 358—are placed near each other. In another embodiment, telemetry link 112 is a far-field radio-frequency telemetry link allowing implantable system 305 and external system 315 to communicate over a telemetry range that is at least ten feet.

Figure 4:
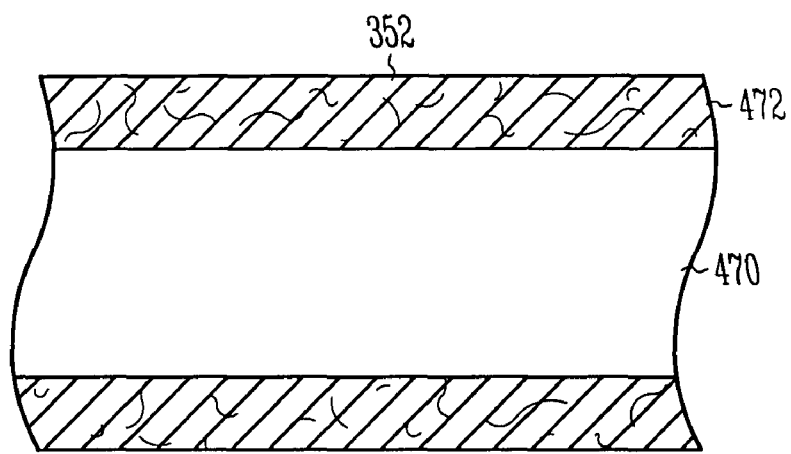
FIG. 4 is an illustration of an embodiment of an implantable cardiovascular device for delivering a biologic therapy.
Figure 5:
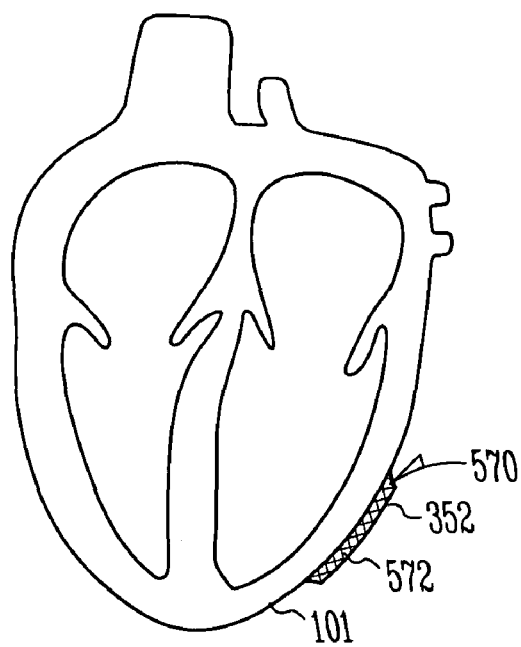
FIG. 5 is an illustration of an embodiment of a cardiac patch for delivering a biologic therapy.

FIGS. 4 and 5 each illustrate an embodiment of an implantable cardiovascular device capable of delivering one or more agents including expression cassette 352. The implantable cardiovascular device includes an implantable device body with at least a cardiovascular portion configured to be placed in the cardiovascular system. Expression cassette 352 is incorporated into the cardiovascular portion of the implantable device body.

FIG. 4 is an illustration of en embodiment of an implantable cardiovascular device having a cardiovascular portion 470. A layer of coating material 472 is coated on cardiovascular portion 470. Expression cassette 352 is embedded in the coating material. Examples of the implantable cardiovascular device include an intravascular stent and an implantable lead having a distal end configured for endocardial or epicardial placement.

FIG. 5 is an illustration of an embodiment of a cardiac patch 570 capable of delivering one or more agents including expression cassette 352. Cardiac patch 570 includes a patch body 572 and expression cassette 352 embedded in patch body 572. Patch body 752 is configured to be placed on a wall of heart 101. In one embodiment, patch body 572 includes an isolated extracellular matrix (ECM) support. An example of the isolated ECM support is discussed in U.S. patent application Ser. No. 11/017,627, entitled "EPICARDIAL PATCH INCLUDING ISOLATED EXTRACELLULAR MATRIX WITH PACING ELECTRODES", filed on Dec. 20, 2004, assigned to Cardiac Pacemakers, Inc., which is incorporated herein by reference in its entirety.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:

1. A cardiac rhythm management system, comprising:
an implantable tachyarrhythmia detection and classification circuit programmed to detect and classify a tachyarrhythmia;
an implantable biologic therapy delivery device comprising an agent delivery device and a gene regulatory signal delivery device, the agent delivery device configured to deliver one or more agents including an expression cassette suitable for transiently terminating or preventing AF, the gene regulatory signal delivery device configured to deliver a regulatory signal carrying a form of energy suitable for regulating the expression cassette;
a composition comprising the expression cassette comprising an energy regulatable transcriptional control element operably linked to a nucleic acid sequence for a gene product, wherein the gene product comprises sequences corresponding to those for an ion channel protein, a connexin, or a fragment thereof, wherein expression from the expression cassette in the atria of the mammal downregulates $I_{Kur}$, $I_{K1}$ or $I_f$ or upregulates connexin expression or activity; and
an implant control circuit coupled to the tachyarrhythmia detection and classification circuit and the biologic therapy delivery device, the control circuit programmed to trigger the delivery of the one or more agents including the expression cassette and the regulatory signal from the biologic therapy delivery device in an amount effective to restore or prolong action potential duration (APD) and/or effective refractory period (ERP) in response to a detection of a tachyarrhythmia classified as AF.

2. The device of claim 1, wherein the expression cassette includes antisense sequences operably linked to a promoter.

3. The device of claim 1, wherein the expression cassette includes an open reading frame encoding a gene product that is atrium-specific.

4. A method to inhibit or treat AF, comprising:
providing a mammal having the system of claim 1; detecting a tachyarrhythmia classified as AF in the mammal; and delivering to the mammal the expression cassette and the regulatory signal in an amount effective to inhibit or prevent AF.

5. The method of claim 4 wherein the expression from the expression cassette alters conduction velocity or effective refractory period (ERP).

6. The method of claim 4 wherein the gene product sequences correspond to those for a protein which forms an ion channel associated with action potential duration, ERP, the Q-T interval, or a combination thereof.

7. The method of claim 4 wherein the gene product encodes a protein associated with $I_{Kur}$, $I_{K1}$ or $I_f$.

8. The method of claim 4 wherein the gene product encodes Cx40, Cx43, or Cx45.

9. The method of claim 4 wherein the gene product is a dominant negative protein, siRNA or an antisense oligonucleotide.

10. The method of claim 4 wherein the expression of the expression cassette prolongs action potential duration, ERP, or both.

11. The method of claim 4 wherein the expression of the gene product alters Kir2.1 expression, Kv1.5 expression or HCN expression in the atria of the mammal.

12. The method of claim 4 wherein the gene product is Kv1.5 siRNA, Kv1.5 antisense RNA or a dominant negative Kv1.5.

13. The method of claim 4 wherein the transcriptional control element is regulated by electromagnetic energy or selected wavelengths of light.

14. The method of claim 4 wherein the transcriptional control element is regulated by a sensed rapid electrical rhythm.

15. The method of claim 4 wherein the expression cassette is systemically administered to the mammal.

16. The method of claim 15 wherein the expression cassette is infused into an artery.

17. The method of claim 4 wherein the expression cassette is injected into the atria of the mammal.

18. The method of claim 4 wherein a viral vector delivers the expression cassette to the mammal.

19. The method of claim 4 wherein the expression cassette is administered to the mammal via a biocompatible material placed on or near the atria of the mammal.

20. The method of claim 19 wherein electrophoresis or photolysis delivers the expression cassette from the biocompatible material to the atria.

21. The method of claim 4 wherein the biologic therapy delivery device is configured to regulate the expression.

* * * * *